(12) United States Patent
Goetz et al.

(10) Patent No.: US 7,247,810 B2
(45) Date of Patent: Jul. 24, 2007

(54) MODULE FOR RESISTANCE WELDING TONGS

(75) Inventors: Eckart Goetz, Erbach (DE); Heinz-Ullrich Mueller, Michelstadt (DE); Reinhard Scholz, Erbach (DE)

(73) Assignee: Bosch Rexroth AG, Stuttgart (DE)

( * ) Notice: Subject to any disclaimer, the term of this patent is extended or adjusted under 35 U.S.C. 154(b) by 139 days.

(21) Appl. No.: 11/001,991

(22) Filed: Dec. 2, 2004

(65) Prior Publication Data

US 2005/0127047 A1    Jun. 16, 2005

(30) Foreign Application Priority Data

Dec. 5, 2003   (DE)   ................. 103 56 978

(51) Int. Cl.
*B23K 11/24* (2006.01)
(52) U.S. Cl. ..................................... 219/110
(58) Field of Classification Search ............... 219/108, 219/109, 110, 113
See application file for complete search history.

(56) References Cited

U.S. PATENT DOCUMENTS

| | | | | |
|---|---|---|---|---|
| 4,577,085 A | * | 3/1986 | Burgher et al. ............. | 219/116 |
| 4,985,612 A | * | 1/1991 | Izume et al. ................ | 219/116 |
| 5,945,011 A | * | 8/1999 | Takano et al. .............. | 219/108 |
| 6,297,467 B1 | * | 10/2001 | Maev et al. ................ | 219/109 |
| 2001/0003800 A1 | | 6/2001 | Crowley | |
| 2002/0134763 A1 | | 9/2002 | Marek et al. | |

OTHER PUBLICATIONS

Patent Abstract of Japan JP 04037480 A, Feb. 7, 1992.

* cited by examiner

*Primary Examiner*—Clifford C. Shaw
(74) *Attorney, Agent, or Firm*—Michael J. Striker

(57) ABSTRACT

The invention originates in the field of resistance welding technology, among other means by means of welding robots 1, for use in roll seam welding, projection welding or spot welding, and has to do with accommodating components for operation inside the housing 2 of the welding tongs. Taking the demands in terms of weight into account, the object of the invention is to achieve the most effective possible utilization of space for the housing 2 of the welding tongs carried by the welding robot. The housing 2 of the welding tongs is given a module 3 for this purpose. This module 3 includes modular components that are relevant to performing the welding process that is monitored by the welding controller.

10 Claims, 2 Drawing Sheets

MODULE FOR RESISTANCE WELDING TONGS

CROSS REFERENCE TO A RELATED APPLICATION

The invention described and claimed hereinbelow is also described in German Patent Application DE 103 56 978.2-34 filed on Dec. 5, 2003. This German Patent Application, whose subject matter is incorporated here by reference, provides the basis for a claim of priority of invention under 35 U.S.C. 119(a)–(d).

BACKGROUND OF THE INVENTION

The invention originates in the field of resistance welding technology for use in roll seam welding, projection welding or spot welding and has to do with accommodating components for the operation inside the welding tongs housing.

In U.S. Patent Application 2002/0134763, a device for attaining various welding currents by means of an inverter of simplified construction is shown, and U.S. Patent Application 2001/0038000 discloses a power unit for a resistance welding system for furnishing the requisite electrical energy, in particular the welding current, for the welding operation by means of an inverter current source.

In Japanese Patent Disclosure JP 04037480 A, the inventor, for reducing costs and for a more-compact design, proposes among other things the integration of a power regulator with a welding transformer. Because of the dimensions of the devices for power regulation in modern resistance welding systems (above all when AC technology is employed), the propose combination nevertheless produces a relatively heavy arrangement that is hard to manipulate and because of its weight and the space it requires would hardly be suitable for being carried along, in the housing of a pair of welding tongs, by a welding robot.

In daily use, however, it often happens that the system comprising the welding tongs and the transformer is mounted movably on a robot arm (welding robot). The weight of this arrangement can rapidly amount to 150 kg or more, and the transformer makes up a substantial proportion of the weight. The weight of the entire arrangement is therefore a decisive factor in dimensioning the mechanics and regulating the motion of the welding robot (joints, carrying capacity, acceleration, etc.), and naturally for the costs to be borne as well. The lower the weight, the less stringent are the demands made of the robot mechanics as well.

Triggering the movable system is often attained locally fixedly in conjunction with a central robot controller.

SUMMARY OF THE INVENTION

Taking the demands in terms of weight into account, the object of the present invention is to attain the most effective possible utilization of space for the welding tongs housing carried by the welding robot, in order on the one hand to gain space in the welding case or control box and on the other to obtain a modular system that is as flexible as possible and does not make excessively stringent mechanical demands of the welding robot, or in other words that meets the requirements for the allowable maximum weight.

By using a smaller, more-sophisticated MF welding transformer of the same power, it was possible to cut the space required, which amounts to only about 30% of a transformer designed for AC technology, and also quite particularly the weight for the MF welding transformer used until now by the present Applicant, virtually in half. Along with the weight saving attained as a result, space is additionally gained in the housing of the welding tongs. This space gained is now occupied according to the invention by a module having a cooled welding transformer with a rectifier, as modular components integrated with the module, and having an interface for furnishing or picking up the electrical input and output variables required for the operation of welding tongs in a resistance welding system equipped with a welding controller, wherein the resistance welding system monitors the welding process, preferably via ultrasonic measurements, and serves in particular to produce weld spots or weld seams on sheet-metal parts in automotive body construction; wherein the module is embodied such that it includes further modular components which are relevant to performing the welding process monitored by the welding controller; the input and output variables of the modular components are exchanged via the interface with welding tongs components, and in particular with electrical drives and ultrasonic transmitters and ultrasonic receivers; and the housing of the welding tongs includes the module. On the one hand, this creates additional stowing space in the control box or welding case and on the other meets the requirements in terms of the desired modularity, because of the existing uniform interface.

The modular components could be made in the form of plug-in cards or boards, for instance, so that similarly to an industrial PC, corresponding functionalities can be retrofitted or replaced, depending on the system configuration.

If a module were advantageously embodied such that it serves to join together welding tongs signals and signals from the transformer sensor analysis and carry them onward, then this module, as an input/output unit, could act as the interface with an externally connected controller or power regulator and communicate with the outside world via standardized interfaces, while inside the welding tongs housing it carries the signals on to the appropriate components.

It would be very particularly advantageous if a relevant modular component is an at least partially integrated device for performing ultrasonic measurements for the sake of testing welded connections and/or for regulating the welding operation. Via a ultrasonic transmitter and a ultrasonic receiver, transverse waves are carried for this purpose through the liquid weld spot during the welding operation. Since liquids, in contrast to solid materials, cannot transmit any transverse forces, the signal received varies as the strength of the melting material decreases. Depending on the varying properties of the weld spot, so-called transmission curves are plotted, from which the instantaneous properties of the weld spot can be read off. That is, a conclusion can be drawn as to whether the melt is too hot, too cold, or at an optimal temperature, for instance. This transmission curve is evaluated by a ultrasonic regulator during the welding operation. From the curve, the instantaneous weld spot diameter can also be calculated, and the data can be evaluated statistically via software, so that in principle any individual weld spot can be recorded. The aforementioned embodiment makes it possible to take the ultrasonic regulator out of the control box and place it directly inside the housing of the welding tongs, or in other words in the direct vicinity of the ultrasonic sensors. Thus the entire generation and/or processing of the ultrasonic measurement data could be attained on-site and without long cable connections. Via a standardized interface, the results of measurement could then be called up directly from a controller. Potential sources of error from cable breakage or transmission errors could be minimized.

If the module is designed such that one or even the single modular component in the module is an at least partially or even fully integrated inverter (or only the power unit), with or without a rectifier, for primary-supply to an MF transformer, then besides the pure MF transformer function, its energy source as well would be accommodated inside the module and hence inside the housing of the welding tongs. Thus the combination of a water-cooled MF transformer with/without a rectifier, together with the inverter, would form a compact, independent unit, which could optionally find a use in other applications as well or could be adopted to other technologies.

A further advantage would be obtained from the at least partial accommodation of devices for regulating the welding current in the module, so that the required space in the control box or welding case, which as a rule is placed on the robot controller, can be reduced or can be eliminated entirely.

Also advantageously, a component for evaluating the sensors of welding tongs motors and/or their triggering for regulating the force and position could be integrated into the module; this would make a further contribution to the modularity of the overall arrangement, and would combine all the components required for using the welding tongs at a central installation site, without long distances. As a rule, in welding tongs, two shafts have to be triggered, for instance by means of electric motors. This triggering could accordingly include two drive regulators, that is, one per shaft. In that case, one shaft takes on the task of tong balancing, while the second shaft carries the electrodes during the welding operation and actuates the pressure cylinder to attain the working stroke or the prestroke during maintenance work. As a connecting member between the motor takeoff section and the tongs, ball revolution spindles are used, in the case of rotationally symmetrical motors. If linear motors are used, a direct drive would also be feasible.

Maximum modularity and economy of space would be assured if a component in the module is an at least partially integrated welding controller, for supporting a controller architecture organized in decentralized fashion, for example. Such operating parameters as the lead time, current time, lag time, and the opening duration could then be specified, among others, by means of this controller.

It is understood that arbitrary combinations of the modular components mentioned above may be combined as needed and depending on the application in such a way that optimal utilization of the existing stowing space in the housing of the welding tongs is obtained. The arrangement is always especially useful whenever devices that act together, such as the ultrasonic sensors and the ultrasonic regulator, or the welding tongs and the welding current regulator, or as already noted the controller as well, are disposed directly in the module. The extent to which a complete integration of all the components relevant to performing the welding process is possible will be determined primarily by the semiconductor technology employed and by the requisite welding currents. Theoretically, full integration would already be conceivable and feasible at present.

To meet customer-specific requirements for various tong functions, the following variants are favored by the present Applicant, as examples:

1. For the fundamental transformer function, the power connection can be made by means of a multi-pin plug or a PG screw fastening. The transformer sensor analysis is carried onward via a terminal or a customer-specific connection, and the possibility exists of combining various tong signals in the module and carrying them to the higher-order controller via a common interface (for instance, via the robot).

2. In addition to the first variant, the function of ultrasonic measurement, with the triggering of the ultrasonic sensor analysis or ultrasonic electronics and the use of a field bus (perhaps CAN) to the inverter, forms one or more modular components of the module.

3. In addition to the first variant, the function of "servo tongs" (regulating the motor performance, processing the sensor analysis pertaining to pressure and the balancing motor, and coding) is integrated into the module.

4. In addition to the third variant, the ultrasonic measurement mentioned in the second variant is integrated as a modular component into the module.

The modular components are advantageously connected electrically to the interface of the module detachably, for instance via plug connections, and thus can be replaced at any time, for instance in the event of repair, and can be removed and introduced quickly and easily.

Because of the often very difficult circumstances in the area surrounding the arrangement, the housing of the module is embodied as impermeable to dust, jets of water, splashing water, or sprayed water (IP65 or IP66 or higher), so as to protect the internal electronics optimally against environmental factors.

Since depending on the type of modular components, cooling may also become necessary, for instance especially if power components are involved, the transformer or rectifier cooling is expanded so that at the same time it dissipates the heat produced by the modular components as well. Because of the increased heat dissipation, however, it may become necessary to increase the coolant throughput, or to replace the coolant itself with a coolant with higher heat absorption.

It is also an attractive option to integrate the energy supply of the module into the module housing as well and to attain a direct voltage via the line voltage, or to use an externally or even internally generated power cycle. This would make a further contribution to integrating the entire system.

The advantage of the invention becomes very particularly apparent when it is employed in a production line for performing an industrial process, in particular for automotive body construction, with welding robots on which welding tongs are mounted in articulated fashion, wherein the welding tongs are operated via a module having a cooled welding transformer with a rectifier, as modular components integrated with the module, and having an interface for furnishing or picking up the electrical input and output variables required for the operation of welding tongs in a resistance welding system equipped with a welding controller, wherein the resistance welding system monitors the welding process, preferably via ultrasonic measurements, and serves in particular to produce weld spots or weld seams on sheet-metal parts in automotive body construction; wherein the module is embodied such that it includes further modular components which are relevant to performing the welding process monitored by the welding controller; the input and output variables of the modular components are exchanged via the interface with welding tongs components, and in particular with electrical drives and ultrasonic transmitters and ultrasonic receivers; and the housing of the welding tongs includes the module, and is carried along during welding.

Decentralized organization and the locating system components outward to the greatest possible extent, using all the reserves of space that are available, is of enormous significance in production lines. The invention helps to reduce the effort and expense for cabling and triggering of the components relevant to the welding operation drastically, and thus to save on expenses. This advantage is still further enhanced by providing that the module is embodied in accordance with one of claims 2 through 11, and/or if all the modules mounted on the welding tongs are connected to a central welding controller and/or a central energy supply.

The fundamental concept of the invention will be explained once again below in conjunction with FIG. 1, and in conjunction with FIG. 2, one possible example of an application is shown highly schematically. In different or the same drawings, the same reference numerals designate identical components.

DESCRIPTION OF THE PREFERRED EMBODIMENTS

The housing 2 of the welding tongs is pivotable in all planes, so that even distant corners, for instance inside an automobile body, can be reached by means of the welding electrodes 12. The electrical supply is assured by means of the module 3, and the module 3 itself communicates in turn with the outside world via the arm of the welding robot, which keeps the requisite supply lines in readiness. Further components that are accommodated in the housing 2 of the welding tongs are not shown here. These include among others electrical drive mechanisms, ball revolution spindles, water-cooled transformers with rectifier diodes, and so forth.

Figure 1:
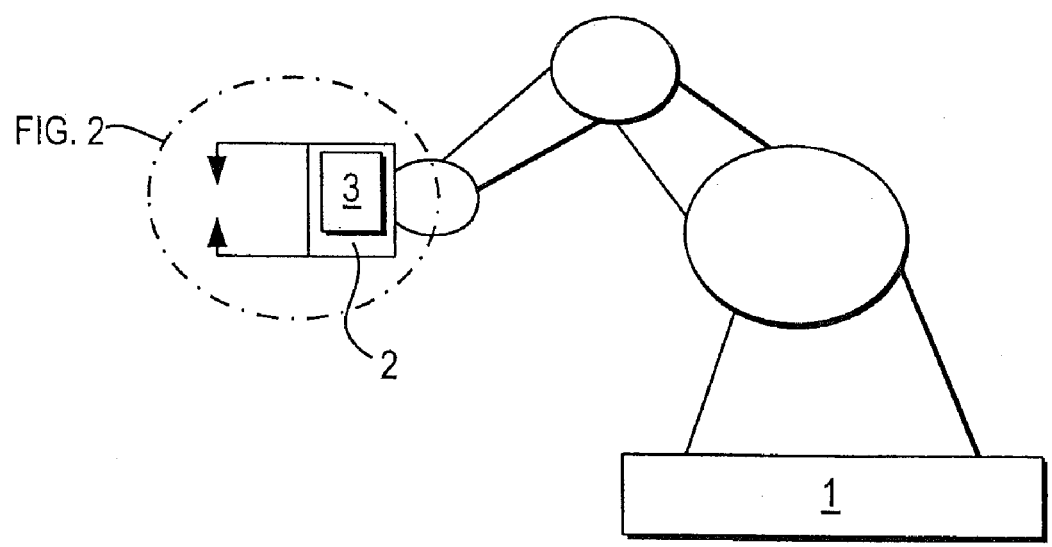
FIG. 1 is a view showing a welding robot with a welding tongs housing and module for resistance welding tongs in accordance with the present invention.
Figure 2:
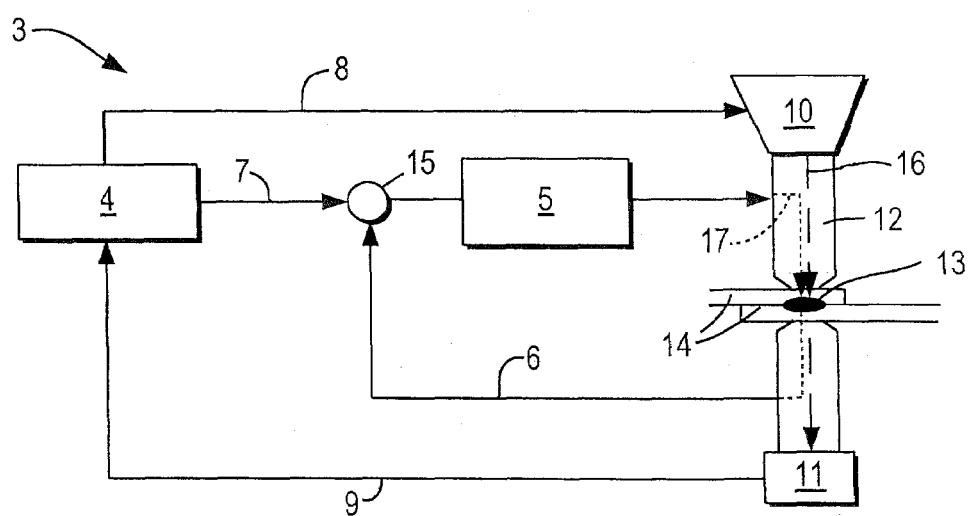
FIG. 2 is a view showing components of the module in accordance with the present invention.

FIG. 2 shows in somewhat more detail what function, for instance by means of the module 3, would be feasible in the housing 2 of the welding tongs. What are shown are a modular component of the module 3, the ultrasonic regulator 4, the current regulator 5, an actual current 6 and set-point current 7 that are delivered to the subtraction circuit 15, the ultrasonic transmission signal 8 and the ultrasonic reception signal 9 with the ultrasonic transmitter 10 and ultrasonic receiver 11, and the welding electrodes 12 and one example of a weld spot 13 for joining the materials 14. The welding current 17 and the transverse waves 16 are also indicated.

As one possible modular component here, the module 3 includes the aforementioned device for performing ultrasonic measurements for testing welded connections during the welding operation. The ultrasonic regulator 4 subjects the ultrasonic transmitter 10 to horizontally polarized transverse waves or shear waves 16. Since liquid materials have no shear resistance, however, shear waves 16 cannot propagate in them, either. Thus the shear waves migrate through the welding tongs, which are mostly produced of copper, into the welding electrodes and then into the liquid weld spot. With increasing liquefication of the welding zone, the characteristic properties of the shear waves carried to the ultrasonic receiver 11 via the electrodes 12 and the welding tongs thus change. This ultrasonic reception signal 9 is received again by the ultrasonic regulator 4 and processed internally. The current regulator 5 receives the set-point current value 7 resulting from this processing and the measured actual current value 6 via the subtraction point 15. Thus a correction signal is available, with which the welding current 17 is adjusted such that it generates a weld spot that meets the requirements, or a temperature that meets the requirements in the weld spot. Other parameters for varying the welded connection would be the contact pressure of the welding electrodes, or the duration of the welding operation. Regulating devices that also affect these variables may additionally be integrated as well. When the invention is employed in a production line, the advantage of the invention is rapidly apparent, since the ultrasonic regulation is now organized in a decentralized fashion, and the provisions for optimizing the welded connection can be performed directly at the location where the weld spot is created.

The invention claimed is:

1. A module for resistance welding tongs provided with welding electrodes, comprising a housing; a current regulator receiving a measured actual current value from the welding electrodes, regulating a current, and supplying an adjusted regulating welding current to the electrodes; an ultrasonic regulator supplying an ultrasonic transmission signal and transmitting it through the welding electrodes and a weld spot, and then receiving an ultrasonic reception signal to generate a set-point current; and processing means receiving said set point current and said actual current value and providing a correction signal supplied to said current regulator for providing the adjusted the welding current supplied to the welding electrodes, said ultrasonic regulator, said current regulator and said processing means being accommodated in said housing.

2. A module as defined in claim 1; and further comprising an ultrasonic transmitter which receives said ultrasonic transmission signal from said ultrasonic regulator and transmits it through the electrodes and the weld spot, and an ultrasonic receiver which receives said ultrasonic reception signal that passed through the electrodes and the weld spot and supplies it to said ultrasonic regulator.

3. A module as defined in claim 1, wherein said processing means include a subtraction point in which subtraction of said set-point current value and said measured actual current value is processed to produce the correction signal.

4. A module as defined in claim 1, wherein said current regulator and said processing means are arranged so that said current regulator supplies the adjusted regulating welding current to one of the electrodes while said processing means receives the measured actual current value from the other of the electrodes.

5. A production line for performing an industrial process, comprising welding robots provided with welding tongs carrying welding electrodes; and modules each provided for a respective one of said welding tongs, each of said modules having a housing, a current regulator receiving a measured actual current value from the welding electrodes, regulating a current, and supplying an adjusted regulating welding current to the electrodes; an ultrasonic regulator supplying an ultrasonic transmission signal and transmitting it through the welding electrodes and a weld spot, and then receiving an ultrasonic receiving signal to generate a set-point current; and processing means receiving said set point current and said actual current value and providing a correction signal supplied to said current regulator for producing the adjusted the welding current supplied to the welding electrodes, said ultrasonic regulator, said current regulator and said processing means being accommodated in said housing.

6. A production line as defined in claim 5, wherein each of said modules has an ultrasonic transmitter which receives said ultrasonic transmission signal from said ultrasonic regulator and transmits it through the electrodes and the weld spot, an ultrasonic receiver which receives said ultrasonic reception signal that passed through the electrodes and the weld spot and supplies it to said ultrasonic regulator.

7. A production line as defined in claim 5, wherein said processing means include a subtraction point in which subtraction of said set-point current value and said measured actual current value is processed to produce the correction signal.

8. A production line as defined in claim 5, wherein said current regulator and said processing means are arranged so that said current regulator supplies the adjusted regulating welding current to one of the electrodes while said processing means receives the measured actual current value from the other of the electrodes.

9. A module for resistance welding tongs provided with welding electrodes, comprising a housing; a current regulator receiving a measured actual current value from the welding electrodes, regulating a current, and supplying an adjusted regulating welding current to the electrodes; ultrasonic means transmitting an ultrasonic signal through the welding electrodes and a weld spot, said current regulator producing the adjusted regulating welding current in response to an ultrasonic signal received after passing through the welding electrodes and the weld spot.

10. A production line for performing an industrial process, comprising welding robots provided with welding tongs carrying welding electrodes; and modules each provided for a respective one of said welding tongs, each of said modules having a housing, a current regulator receiving a measured actual current value from the welding electrodes, regulating a current, and supplying an adjusted regulating welding current to the electrodes, ultrasonic means transmitting an ultrasonic signal through the welding electrodes and a weld spot, said current regulator producing the adjusted regulating welding current in response to an ultrasonic signal received after passing through the welding electrodes and the weld spot.

* * * * *